United States Patent
Emmerson et al.

(10) Patent No.: US 7,541,573 B2
(45) Date of Patent: Jun. 2, 2009

(54) OPTICAL SENSORS FOR SENSING THE REFRACTIVE INDEX OF FLUID SAMPLES

(75) Inventors: Gregory Daniel Emmerson, Highfield (GB); Corin Barry Edmund Gawith, Highfield (GB); Peter George Robin Smith, Highfield (GB)

(73) Assignee: University of Southampton, Southampton (GB)

( * ) Notice: Subject to any disclaimer, the term of this patent is extended or adjusted under 35 U.S.C. 154(b) by 158 days.

(21) Appl. No.: 11/572,125

(22) PCT Filed: Jul. 7, 2005

(86) PCT No.: PCT/GB2005/002682

§ 371 (c)(1),
(2), (4) Date: Jan. 15, 2007

(87) PCT Pub. No.: WO2006/008448

PCT Pub. Date: Jan. 26, 2006

(65) Prior Publication Data

US 2008/0043242 A1    Feb. 21, 2008

(30) Foreign Application Priority Data

Jul. 15, 2004    (GB)    ................ 0415882.0

(51) Int. Cl.
*G01J 5/08*    (2006.01)
*G02B 6/00*    (2006.01)
*G01N 21/41*    (2006.01)

(52) U.S. Cl. ................. 250/227.18; 385/12; 356/128

(58) Field of Classification Search ............ 250/227.11, 250/227.14, 227.18; 385/12; 356/128
See application file for complete search history.

(56) References Cited

U.S. PATENT DOCUMENTS 5,305,071 A    4/1994    Wyatt (Continued)

FOREIGN PATENT DOCUMENTS

GB    2 395 797    6/2004

(Continued)

OTHER PUBLICATIONS

Schroeder et al., "A fibre Bragg grating reflectometer", Jul. 2001, Meas. Sci. Technol. 12, pp. 757-764.*

(Continued)

*Primary Examiner*—Thanh X Luu
(74) *Attorney, Agent, or Firm*—Renner, Otto, Boisselle & Sklar LLP (57)    ABSTRACT

An optical sensor comprises a sensing element comprising a waveguide grating with a response that varies with an effective modal index experienced by light propagating in the grating and a sample window for receiving fluid which affects the effective modal index to modify the response, the sensing element arranged to receive light from a light source and to output the light after filtering; and an analyzing element comprising a second waveguide grating having a second response, and arranged to receive light output by the sensing element and to output the light after filtering for detection by an optical power detector. The combination of the two gratings converts changes in the wavelength of light output by the sensing element in response to the sample of fluid to changes in the amount of light, allowing the fluid index to be deduced from a measurement of optical power. The two elements may be fabricated on a single substrate to reduce errors from environmental disturbances such as temperature changes.

31 Claims, 5 Drawing Sheets

U.S. PATENT DOCUMENTS

| | | | | |
|---|---|---|---|---|
| 5,380,995 | A | * | 1/1995 | Udd et al. ............... 250/227.18 |
| 5,494,829 | A | | 2/1996 | Sandstrom et al. |
| 5,631,171 | A | | 5/1997 | Sandstrom et al. |
| 5,896,484 | A | | 4/1999 | Borrelli et al. |
| 6,650,799 | B2 | * | 11/2003 | Lyons .......................... 385/12 |

FOREIGN PATENT DOCUMENTS

WO          9509355          4/1995

OTHER PUBLICATIONS

J Bowen, LJ Noe, BP Sullivan, K Morris, V Martin and G Donnelly, "Gas phase detection of trinitrotoluene utilizing a solid-phase antibody immobilized on a gold film by means of surface plasmon resonance spectroscopy", Appl. Spectrosc., 57(8), 906-914, 2003.

RG Heideman, RPH Kooyman and J Greve, "Performance of a highly sensitive optical wave-guide Mach-Zehnder interferometer immunosensor", Sensors and Actuators B-Chemical, 10(3), 209-217, 1993.

K Tiefenthaler and W Kukosz, "Integrated optical switches and gas sensors", Optics Letters, 10(4), 137-139, 1984.

W Lukosz, D Clerc and PhM Nellen, "Input and output grating couplers as integrated optical chemo- and biosensors", Sensors and Acuators A, 25-27, 181-184, 1991.

A Asseh, S Sandgren, H Ashlfeldt, B. Sahlgren, R Stubbe and G Edwall, "Fiber optical Bragg grating refractometer", Fiber and Integrated Optics, 17(1), 51-62, 1998.

A Iadicicco, A Cusano, A Cutolo, R Bernini and M Giordano, "Thinned fiber Bragg gratings as high sensitivity refractive index sensor", IEEE Photonics Technology Letters, 16(4), 1149-1151, Apr. 2004.

X Chen, K Zhou, L Zhang and I Bennion, "Optical chemsensors utilizing long-period fiber gratings UV-inscribed in D-fiber with enhanced sensitivity through cladding etching", IEEE Photonics Technology Letters, 16(5), 1352-1354, May 2004.

BJ Luff, JS Wilkinson, G Perrone, "Indium tin oxide overlayered waveguides for sensor applications", Applied Optics, 36(27), 7066-7072, 1997.

W Lukosz, "Integrated optical chemical and biochemical sensor", Sensors and Actuators B, 29, 37-50, 1995.

MQ Bu, M Tracy, G Ensell, JS Wilkinson, AGR Evans, "Design and theoretical evaluation of a novel microfluidic device to be used for PCR", Journal of Micromechanics and Microengineering, 13(4), S125-S130, 2003.

R Kashyap, "Photosensitive optical fibers: Devices and applications", Optical Fiber Technology, 1, 17-34, 1994.

* cited by examiner

OPTICAL SENSORS FOR SENSING THE REFRACTIVE INDEX OF FLUID SAMPLES

This application is a national phase of International Application No. PCT/GB2005/002682 filed Jul. 7, 2005 and published in the English language.

BACKGROUND OF THE INVENTION

The present invention relates to optical sensors, particularly but not exclusively to optical sensors based on planar waveguide gratings for sensing the refractive index of fluid samples and parameters and characteristics related thereto.

Measurement of the optical refractive index of fluids is of importance in fields including bioanalysis and biosensing. Different fluids, or concentrations of the same fluid, have different refractive indices so that the fluids can be identified or distinguished from refractive index measurements. The refractive index or change in refractive index of a fluid can be used to determine many biologically important measurands such as protein concentrations and glucose levels. In other fields, refractive index measurements are used in applications as diverse as process control and the detection of explosives [1].

Various devices and techniques for measuring refractive index are known. These include the Abbe-type refractometer, and sensors based on surface plasmon resonance. Optical waveguides may also be used. The presence of a liquid adjacent to an optical waveguide can alter the effective modal index of light propagating within the waveguide. This modification of index can be measured using techniques that are sensitive to changes in optical path length. For example, interferometer structures have been used to measure index changes and hence to sense the presence of proteins [2].

An alternative to interferometric measurement is to use optical waveguide gratings, where the reflective properties of a grating, which depend on refractive index, are modified by the index of a liquid in contact with the waveguide. An early device of this type used planar optical waveguides with surface relief gratings, in which adsorption and desorption of gas on the waveguide surface changed the refractive index and allowed the gas to be sensed [3]; other planar grating configurations have been proposed for integrated optical biological and chemical sensors [4]. Other grating-based devices have used fibre Bragg gratings [5]. Proposals have included thinning of the fibre with wet-etching to increase sensitivity [6], and the use of long period gratings in D-fibre, found to be more sensitive than gratings in standard telecom fibre [7]. However, the use of fibre gratings requires tedious working of the fibre to expose the waveguiding core to the liquid, such as by etching, which is difficult to control in a fibre geometry, or mounting the fibre in a block and polishing it down to access the core. Planar waveguide implementations are preferable in that it is typically easier to gain access to the propagating optical mode.

SUMMARY OF THE INVENTION

A first aspect of the present invention is directed to an optical sensor comprising: a sensing element comprising a first wavelength selective filter having a first wavelength filtering response that varies with an effective modal index experienced by light propagating in the filter and a sample window arranged to receive a sample of fluid such that the presence of a sample of fluid affects the effective modal index experienced by light propagating in the filter and hence modifies the first wavelength filtering response; the sensing element arranged to receive light from a light source and to output the light after filtering; and an analysing element comprising a second wavelength selective filter having a second wavelength filtering response, and arranged to receive light output by the sensing element and to output the light after filtering for detection by an optical power detector.

By passing light through first a sensing element and then an analysing element, the filtering effects of the two elements are combined. This transforms the wavelength-dependent response of the sensing element to a fluid sample into an intensity-dependent response, so that a simple optical power measurement is sufficient to determine the index change wrought by the fluid sample and hence the index of the sample, in place of the spectral measurements required by conventional devices. This makes for less complex, more compact and cheaper sensors. The output can be tailored by selecting particular shapes of first and second wavelength filtering response, to give a linear output for example.

The filtering can be performed in reflection or transmission, which offers further choice in tailoring the sensor output via the shapes of the filtering responses, and offers flexibility in the way in which the sensing and analysing elements are linked together. The sensing element may be arranged such that it outputs light that has been filtered by reflection from the first wavelength selective filter, or such that it outputs light that has been filtered by transmission through the first wavelength selective filter. Similarly, the analysing element may be arranged such that it outputs light that has been filtered by reflection from the second wavelength selective filter, or such that it outputs light that has been filtered by transmission through the second wavelength selective filter.

In some embodiments, the analysing element further comprises a reference window arranged to receive fluid such that the presence of fluid affects an effective modal index of light propagating in the second wavelength selective filter and modifies the second wavelength filtering response. This arrangement offers at least partial protection from environmental influences that may perturb the response of the sensing element. The two windows allow the environments of the two elements to be matched so that the same perturbations occur to each. The difference between the responses of the two elements is thus limited to the index difference of the fluid sample and the reference fluid, which can thus be more accurately determined.

The sensing element and the analysing element may comprise planar waveguides containing gratings of periodic refractive index change that define the wavelength selective filters. Planar waveguide gratings are a particularly convenient way of providing the required filtering responses, since they can be fabricated accurately with a wide range of responses, and are compact and robust. Advantageously, the waveguides are configured for single mode propagation of light.

In the case of grating elements, the sample window may overlie the grating of the sensing element and comprise a portion of a cladding layer overlying a core of the waveguide of the sensing element, such that a sample of fluid received by the sample window is in contact with the cladding layer. Alternatively, the sample window may overlie the grating of the sensing element and comprise an exposed portion of a core of the waveguide of the sensing element, such that a sample of fluid received by the sample window is in contact with the core. These alternatives can be used to select the sensitivity of the sensing element to the fluid, with further flexibility available in the former alternative by choosing the thickness of the cladding layer to determine the proximity of the fluid to the core. In the latter alternative, the exposed portion of the core may have a thickness less than a thickness of the core in adjacent portions of the waveguide of the sensing element. This arrangement can be used to give single mode waveguiding through the sensing element to overcome modal disturbance that can arise from the change of waveguide structure at the edges of the sample window.

Also, a core of the waveguide of the sensing element may have a tapering variation in refractive index along its length, to reduce abrupt changes in the effective model index between the exposed portion of the core and adjacent portions of the core. A waveguide structured in this way also helps to overcome modal disturbances at the window boundaries, by reducing reflections that may occur at an abrupt structural boundary.

The waveguide of the sensing element may comprise one or more layers that modify waveguiding properties of the waveguide. Additional layers can be used to pull the optical field of light propagating in the waveguide towards or away from the sample window, allowing tailoring of the sensitivity of the sensor to fluid received in the window.

Sensors according to the present invention may be used to make direct refractive index measurements, or to measure or detect fluid characteristics that vary with refractive index. This approach can be extended by simple modifications to the sensor. For example, the sample window may provided with a surface coating of a chemically selective material operable to bind with molecules that may be present in a sample of fluid to be received by the sample window, the binding causing an alteration of the effective modal index. Thus, chemically and biochemically reactive substances can be detected, for example, testing for the presence of particular antibodies in biological samples. Alternatively, the sample window may be provided with a surface layer of a metal having a surface plasmon that may be altered by a sample of fluid to be received by the sample window, the alteration in the surface plasmon causing an alteration of the effective modal index.

In some embodiments, the optical sensor may further comprise: a substrate on which the sensing element and the analysing element are positioned; an input waveguide defined on the substrate and arranged to deliver light from a light source to the sensing element; a connecting waveguide defined on the substrate and arranged to deliver light output by the sensing element to the analysing element; and an output waveguide defined on the substrate and arranged to deliver light output by the analysing element for detection by an optical power detector. Placing the two elements on the same substrate is particularly advantageous since they will have more similar environments so that the output of the sensor is less subject to errors caused by disturbances to only one of the elements. Also, the fabrication and structure of the sensor is simplified; direct ultraviolet writing techniques can be used to define the components of the whole sensor in a single processing step.

The connecting waveguide may be arranged to deliver a portion of light output by the sensing element to the analysing element and further arranged to deliver a portion of light output by the sensing element for detection by an optical power detector. This "tap" can be used to identify and compensate for optical losses occurring in the sensor that would otherwise appear as a reduced output power and corresponding erroneous measurement.

The optical sensor may further comprise a heater operable to modify the temperature of the sensing element and the analysing element such that the sensing element and the analysing element have substantially the same temperature. Measurements can be made at different fluid temperatures by heating the sensing element and the fluid sample. The fact that the analysing element is similarly heated eliminates errors that could otherwise arise if the wavelength filtering responses are temperature-dependent (such as is the case for waveguide gratings), since both elements undergo the same temperature-induced change which is hence cancelled from the overall sensor output.

The optical sensor may further comprise one or more fluid flow control elements positioned on the substrate and operable to supply fluid to and/or remove fluid from the sample window. Advantageously, the fluid flow control elements are micro-electro-mechanical systems (MEMS) devices. Such elements can be used to enhance and/or automate fluid supply and removal, or allow measurements to be made on a continuous flow of fluid.

The present invention is not limited to embodiments including a single sensing element and a single analysing element. According to many embodiments, the optical sensor further comprises one or more additional sensing elements positioned on the substrate, each additional sensing element having an associated analysing element positioned on the substrate and associated input, connecting and output waveguides defined on the substrate. The provision of extra elements allows many configurations of sensor to be implemented, offering simultaneous testing of multiple samples or testing under different parameters. For example, each sensing element may have a substantially identical first wavelength filtering response. This allows simultaneous testing of different fluid samples under the same test conditions. Alternatively, each sensing element or group of sensing elements may have a different first wavelength filtering response, for example the different first wavelength filtering responses may have different centre wavelengths. This allows testing of samples of the same fluid (or of different fluids if desired) at different wavelengths, so that the dispersion of a fluid can be measured, for example.

Additionally or alternatively, each sensing element may comprise a planar waveguide containing a grating of periodic refractive index change that defines the first wavelength selective filter of that sensing element, and the sample window of each sensing element overlies the grating of that sensing element and comprises a portion of a cladding layer overlying a core of the waveguide of that sensing element, such that a sample of fluid received by the sample window is in contact with the cladding layer, in which the portion of the cladding layer of each sensing element or group of sensing elements has a different thickness. This configuration offers an array of sensing elements of different sensitivity.

In the event that a sensor is intended for simultaneous testing of the same fluid under different wavelength and/or sensitivity conditions, the sensing elements may comprise a single sample window shared by the sensing elements such that a sample of fluid received by the single sample window modifies the wavelength filtering response of each sensing element.

The optical sensor may comprise sensing and analysing elements according to the preceding examples and embodiments, to which a user can connect light sources and optical power detectors as required. However, other embodiments may additionally include these components, perhaps mounted on a single substrate with the sensing and analysing elements. Therefore, the optical sensor may further comprise one or more light sources operable to deliver light to the or each sensing element such that the or each sensing element receives light having a spectral bandwidth covering at least part of its first wavelength filtering response. The one or more light sources may comprise a single light source. Also, the optical sensor may further comprise an optical power detector operable to detect the optical power of light output by the or each analysing element.

A second aspect of the present invention is directed to a method of measuring refractive index comprising: placing a sample of fluid having a refractive index in proximity to a first wavelength selective filter having a first wavelength filtering response that varies with an effective modal index experienced by light propagating in the filter and is modified by the presence of the sample of fluid; applying light to the first wavelength selective filter to obtain an output of light filtered by the first wavelength selective filter; applying the light output by the first wavelength selective filter to a second wavelength selective filter having a second wavelength filtering response to obtain an output of light filtered by the second wavelength selective filter; making an optical power measurement of the light output by the second wavelength selective filter, the optical power being proportional to the refractive index of the sample of fluid; and deducing the refractive index of the sample of fluid from the optical power measurement.

The method may further comprise deducing a characteristic of the sample of fluid from the deduced refractive index where that characteristic is related to refractive index.

BRIEF DESCRIPTION OF THE DRAWINGS

For a better understanding of the invention and to show how the same may be carried into effect reference is now made by way of example to the accompanying drawings in which.

DETAILED DESCRIPTION

An optical reflective grating such as a Bragg grating comprises a periodic modification of refractive index within an optical waveguiding structure, where the waveguiding structure comprises a core surrounded by a cladding material of a lower refractive index than the core. This structure guides optical waves by total internal reflection at the boundary between the two refractive indices. The grating reflects light propagating along the waveguide of wavelengths that falls within a bandwidth defined by the magnitude and dimensions of the periodic refractive index modification, and transmits light of other wavelengths.

If a region of the core of the waveguide is exposed or nearly exposed by removing all or part of a portion of the cladding, and a fluid applied to the region so that the optical field of light propagating in the waveguide extends into the fluid, the refractive index of the fluid modifies the effective modal index experienced by the propagating light. This is turn modifies the reflectivity properties of the grating, which can be measured. From this measurement, the refractive index of the fluid can be determined, which allows either direct refractive index measurements to be made, or other properties of the fluid to be determined if the relationship between these properties and refractive index is known.

A Bragg grating has a reflectivity peak at a wavelength $\lambda_{Bragg}$. This is defined by the Bragg relation $$n_{eff} = \lambda_{Bragg}/2\Lambda$$

where $n_{eff}$ is the effective modal index and $\Lambda$ is the grating period. Thus, if the grating period is known and the peak reflected wavelength is measured, the effective modal index can be calculated using the Bragg relation. From this, the refractive index of the fluid can be ascertained by calculation or by reference to the measured properties of calibrated standard liquids.

To achieve this, it is necessary to make accurate measurements of the wavelength of light reflected from or transmitted by the grating. Thus, a photodetecting device with adequate spectral resolution is required; these tend to be costly and bulky, and the resolution of the device will impact on the resolution of the measurements that can be made.

The present invention seeks to address this issue by removing the requirement for spectrally resolved measurements. This is done by passing light output by the first grating through a second grating, and measuring the light output by the second grating. This converts the change in reflected wavelength of the first grating into a change in intensity, as will be described below. Intensity can be readily and accurately measured using simple devices such as photodiodes, so that the measurement of refractive index is improved and simplified.

Figure 1:
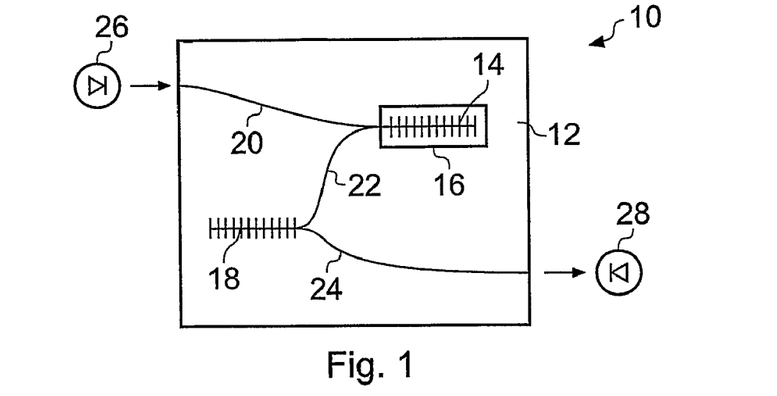
FIG. 1 shows a schematic representation of an optical sensor according to an embodiment of the present invention.

FIG. 1 shows a schematic plan view representation of an example of a first embodiment of an optical sensor for sensing refractive index according to the present invention. The optical sensor 10 is formed on a single substrate 12, into which two planar waveguide gratings and associated waveguides are written. The first grating, or sensing grating 14, has a sample window 16 over it, which is a region of the substrate in which some or all of the cladding that defines the waveguiding properties is removed. A sample of fluid can be thereby be applied to the sensing grating by placing it in the sample window. The second grating, or analyser grating 18, has no such window in this embodiment.

The sensing grating 14 and the analysing grating 18, themselves defined within waveguides, are connected by channel waveguides defined on the substrate 12. An input waveguide 20 carries light generated by an optical source 26 to the sensing grating 14. A connecting waveguide 22 carries light reflected from the sensing grating 14 to the analysing grating 18. An output waveguide 24 carries light reflected from the analysing grating 18 and delivers it for detection by an optical power detector 28, such as a photodiode.

Figure 2A:
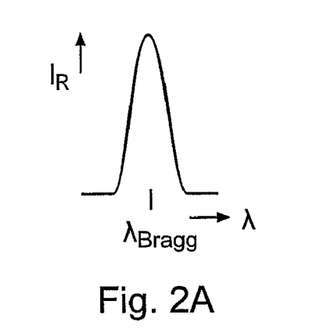
FIGS. 2A to 2E show example wavelength filtering responses of gratings included in the optical sensor of FIG. 1, demonstrating the operation of the sensor.

The two gratings each have a reflectivity/transmissivity function that allows them to operate as narrow-band optical filters, reflecting only light with wavelengths that satisfy the Bragg relation. These functions can be thought of as wavelength filtering responses. FIG. 2A shows the response of the sensing grating 14 as a plot of wavelength λ against reflected intensity $I_R$; this is the light that will be reflected from the sensing grating if it is illuminated by light with a bandwidth broad enough to cover the bandwidth of the response peak. Thus, the optical source 26 is chosen to generate light of an appropriate spectral bandwidth. A light emitting diode may be suitable. A general broadband source may also be used.

Operation of the sensor depends on shifting of the Bragg wavelength of the sensing grating 14, so the optical source should be further chosen to have an output with a bandwidth that encompasses the magnitude of the expected shift; this will depend on the range of fluids to be sensed by the sensor.

Figure 2B:
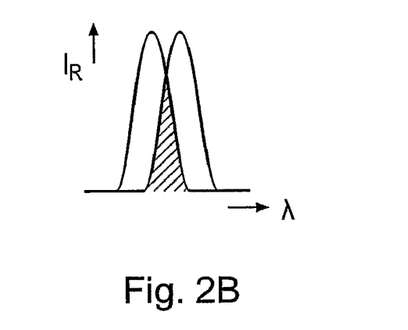

As explained, the sensing grating 14 has had some or all of its overlying cladding removed to allow the effective modal index to be affected, or altered, by the presence of a sample of fluid received by the sample window 16. In this example, the analysing grating 18 is left fully cladded so that it is isolated from the variable to which the sensing grating 14 is exposed. Also in this example, the analysing grating 18 is chosen to have a response of the same shape as the response of the sensing grating 14, but which, in the absence of fluid applied to the sample window, is offset from it by half the bandwidth of the sensing grating at the centre of the operation sensing range. FIG. 2B shows the two responses.

In operation, light from the optical source 26 is delivered to the sensing grating 14 and some is reflected in accordance with the wavelength filtering response of the sensing grating and delivered to the analysing grating 18. Light reflected from the analysing grating 18 is delivered to the optical power detector 28 for detection.

The amount of light detected after reflection by both gratings is determined by the overlap of the two grating responses, indicated by the shaded area in FIG. 2B. The application of fluids with different refractive indices to the sample window 14 causes a change in the effective modal index of the sensing grating, which shifts the Bragg wavelength of the sensing grating. Thus, the amount of overlap between the two wavelength filtering responses also changes, altering the amount of light delivered to the optical power detector. The wavelength shift of the first grating is converted into an intensity shift by the second grating. Consequently, the amount of measured optical power is directly related to the refractive index of the fluid, so that the refractive index of a sample received by the sample window can be determined following appropriate calibration of the optical sensor 10. This arrangement allows the output of the sensor to be detected using a non-spectrally dependent optical detector such as a photodiode. The output power is directly dependent on the highly spectrally sensitive wavelength shift from the sensing grating, so that very accurate measurements can be simply made.

Figure 2C:
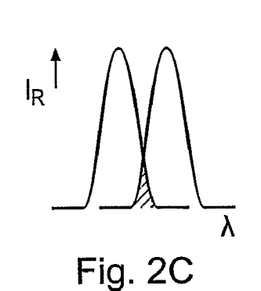
Figure 2D:
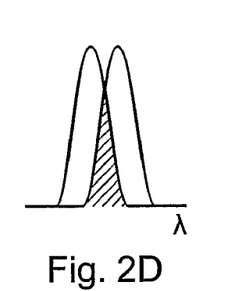
Figure 2E:
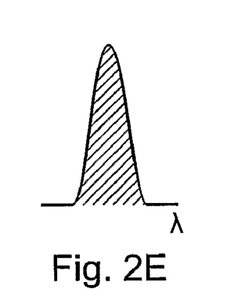

FIGS. 2C to 2E illustrate the changing output of the sensor 10 in response to fluids of different refractive index. In FIG. 2C, a fluid with a large index n1 is measured; this increases the modal index and hence the Bragg wavelength so that the wavelength reflectivity responses of the two gratings shift apart. The overlap is reduced, and a smaller power level is detected. In FIG. 2E, a fluid with a small index n3 is measured, which has the opposite effect of shifting the responses closer together and increasing the overlap so that more power is detected. FIG. 2D shows the intermediate position, where little change in index is caused by the fluid.

Figure 3:
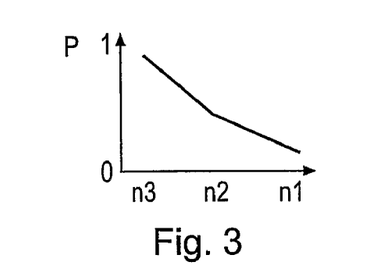
FIG. 3 shows an example graph illustrating the output of the optical sensor of FIG. 1, being a plot of measured output power as a function of fluid refractive index.

FIG. 3 shows a graph of the variation of optical power P output by the sensor with refractive index of the fluid. As expected, the power decreases with increasing index (n3 to n1). A curve of this type can be generated using a range of fluids with known index and used as a calibration curve, allowing the index of any sample to be determined directly from the measured power.

Figure 4A:
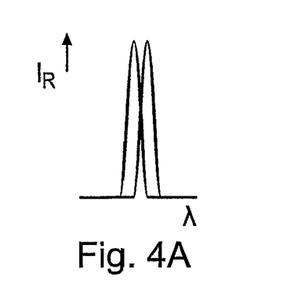
FIGS. 4A and 4B show further example wavelength filtering responses of gratings that may be used to implement embodiments of the invention.
Figure 4B:
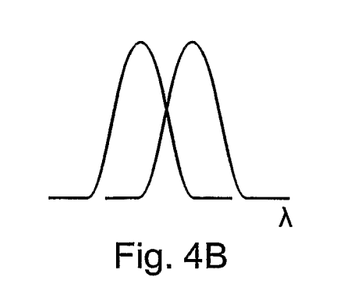

The sensitivity and functional range of the optical sensor is a function of the wavelength filtering responses of the gratings. Very small bandwidth gratings provide high sensitivity over a small wavelength range, since the amount of overlap changes rapidly with index, whereas broad gratings provide less sensitivity over a wider range. FIGS. 4A and 4B respectively illustrate examples of these alternatives.

Figure 5:
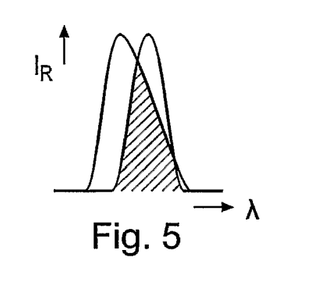
FIG. 5 shows a further example of wavelength filtering responses of gratings that may be used to implement embodiments of the invention.

The spectral shape of the grating responses is not limited to the simple shapes shown in the examples so far. A more complex response, with sidebands, for example, would function. Square grating profiles provide a wide wavelength range of operation combined with a high degree of sensitivity (since sensitivity is the function of rate of change of overlap with wavelength shift). Non-uniform grating structures (with non-constant period and/or grating strength) can be used to tailor the grating responses so as to give a linear relationship of output power to wavelength shift/refractive index. Asymmetric responses can be used to avoid the double-valued nature of the output function produced by symmetric responses such as those shown in FIGS. 2 and 4 that will arise if the wavelength shift moves the sensing grating response past the mid-point of the analysing grating response. Also, the responses of the two gratings need not be the same shape. Gratings with differently shaped profiles and/or different bandwidths can be used together, as shown in FIG. 5.

Figure 6:
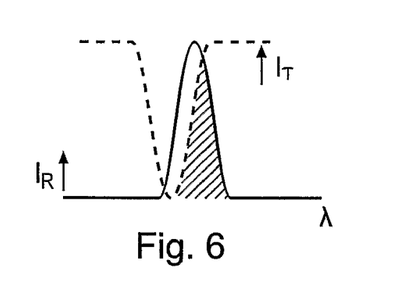
FIG. 6 shows a yet further example of wavelength filtering responses of gratings that may be used to implement embodiments of the invention.

Furthermore, either or both of the gratings can be used in transmissive mode instead of reflective mode. Operation of the sensor remains the same, with the output power being determined by the overlap in the wavelength filtering responses of the two gratings, which is determined by the wavelength shift in the sensing grating response produced by the fluid sample. Two gratings used in transmission will give an output equivalent to that described so far for two reflecting gratings, since the transmission profile is the inverse of the reflection profile. For one grating in transmission and one in reflection, an example of the overlapping wavelength responses are shown in FIG. 6. For the transmission grating the output is the transmitted intensity $I_T$ and for the reflection grating the output is the reflected intensity $I_R$; as before, the shaded overlap shows the power output by the combination of the two gratings, proportional to the index of the fluid. Either of the two gratings may be the transmission grating.

Figure 7A:
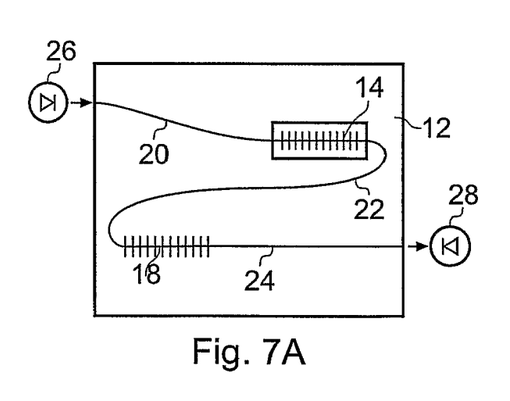
FIGS. 7A, 7B and 7C show schematic representations of optical sensors according to further embodiments that use gratings in different transmissive and reflective configurations.
Figure 7B:
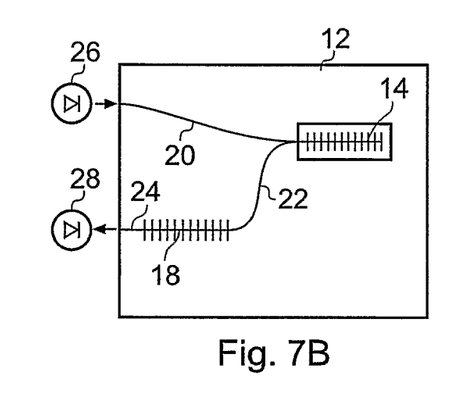
Figure 7C:
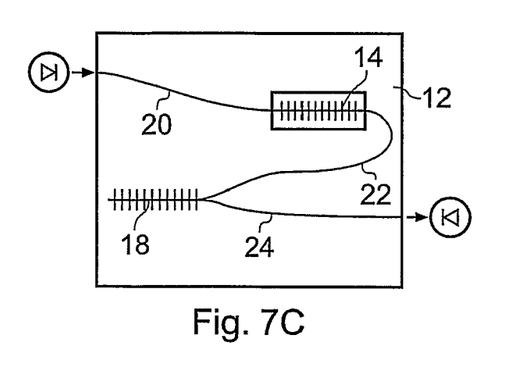

FIGS. 7A, 7B and 7C show schematic plan view representations of optical sensors embodying these alternatives. FIG. 7A shows both the sensing grating 14 and the analysing grating 18 arranged for use in transmission, so that the output of the sensing grating 14 delivered to the analysing grating 18 by the connecting waveguide 22 is that part of the light from the optical source 26 transmitted through the sensing grating 14, and the output of the analysing grating 18 delivered to the detector 28 by the output waveguide 24 is that part of the light from the sensing grating 14 transmitted through the analysing grating. FIG. 7B shows the sensing grating 14 used in reflection with the analyser grating 18 used in transmission, and FIG. 7C shows the sensing grating 14 used in transmission while the analysing grating 18 is used in reflection.

The example sensors shown thus far each have a sample window over the sensing grating to receive a sample of fluid to be measured, and no window over the analysing grating. However, in alternative embodiments, a further window, referred to as a reference window, preferably of the same structure as the sample window, is provided over the analysing grating. This allows a known reference fluid such as an aqueous solution to be applied to the analysing grating. The aim of this to make the environment of the analysing grating as like as possible to that of the sensing grating so that any perturbation (such as a temperature change) other than application of the fluid sample to the sensing grating that results in a shift in the Bragg wavelength of the gratings is substantially the same for each grating and hence does not affect the output power of the sensor.

Figure 8:
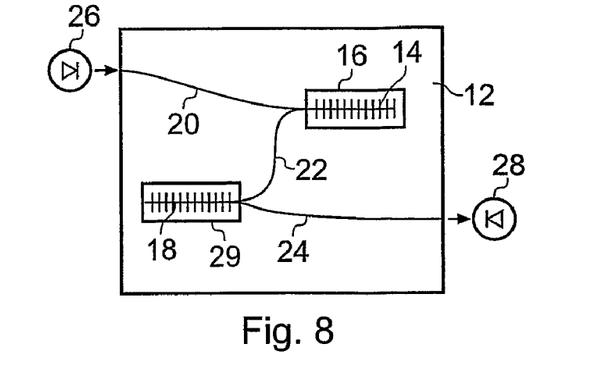
FIG. 8 shows a schematic representation of an optical sensor according to a further embodiment that includes a window for applying a reference fluid to the sensor.

FIG. 8 shows a schematic plan view representation of an example sensor that incorporates a reference window 29 over the analyser grating 18. The structure of the sensor is otherwise the same as that shown in FIG. 1.

The embodiments discussed thus far are each fabricated on a single substrate. Although this is not essential, it is considered to be advantageous in that the two gratings have the same environment and hence experience substantially the same response to external variables that can cause a shift in the Bragg wavelength. Shifting of this kind, occurring in response to variables other than the sample fluid, is a problem with known grating index sensors comprising only one grating. The two-grating configuration of the present invention addresses this. Any temperature, stress or other perturbations that can cause changes in the grating period and hence in the Bragg wavelength occur to both gratings. Thus, the wavelength filtering responses of both gratings are affected in the same way and the overlap that is of interest depends only on the fluid sample. Thus the unwanted effects of external variables are compensated for and their impact reduced or eliminated.

Further in this regard, it is possible to introduce temperature as a desirable variable into the index measurements. A heater such as a heating element or similar can be thermally coupled to the optical sensor. Heat can be applied to change the temperature of the fluid sample. The sensing grating and the analysing grating also experience a change in temperature, which affects the grating periods and Bragg wavelengths, but since the gratings are on the same substrate coupled to the same heater, each experiences substantially the same temperature change and shift in wavelength filtering response. Thus, the optical output power of the sensor depends only on the refractive index of the sample of fluid in the sample window. Refractive index typically varies with temperature, so that the heater can be used to heat the fluid to a selection of known temperatures or through a temperature cycle while measurements of its index are made, to yield the rate of change of index with temperature, dn/dT. Also, different fluids can be distinguished, since even if they have identical refractive indices at one or more temperatures, they are unlikely to have the same temperature dependence of index. Further, particular heat-dependent stages in chemical and biological reactions can be identified.

Figure 9:
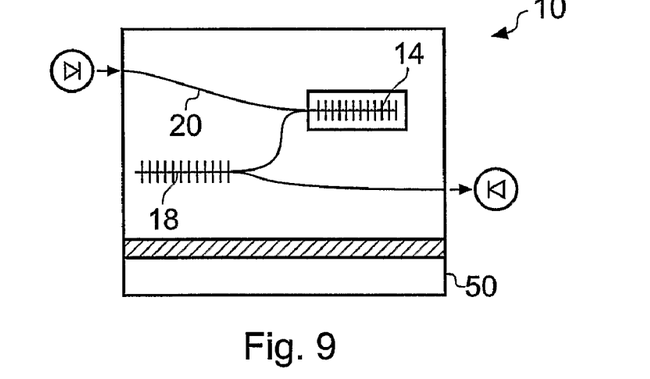
FIG. 9 shows a schematic representation of an optical sensor according to a further embodiment that includes a heater.

FIG. 9 shows a schematic plan view representation of the optical sensor 10 of FIG. 1 that has been augmented with a heater 50 in the above manner. To achieve good results using this technique, the heater should be coupled to the optical sensor so as to give provide the same heating effect to both gratings, and preferably to the whole substrate, to eliminate any temperature variation between the gratings that could affect the index measurements.

Figure 10:
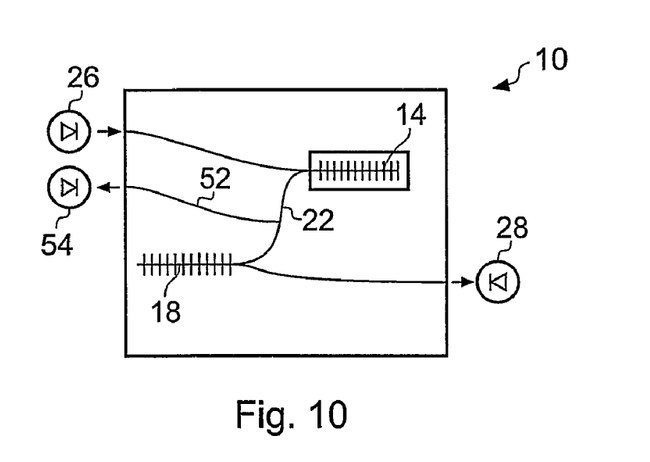
FIG. 10 shows a schematic representation of an optical sensor according to a further embodiment that includes features allowing compensation for optical loss.

Further embodiments of the present invention are intended to improve operation of the optical sensor by allowing compensation for optical loss. FIG. 10 shows a schematic representation of a optical sensor 10 configured for this. The sensor 10 corresponds in all respects with the sensor 10 of FIG. 1, but additionally includes an extra branch 52 to the connecting waveguide 22 that takes the output of the sensing grating 14 to the analyser grating 18. The branch 52 delivers a known portion of the output of the sensing grating 14 to a further optical power detector 54, while the remainder of the output is delivered to the analysing grating 18. Power measurements made using the further detector 54 can be compared with those made using the main detector 28 and/or the expected output power of the light source 26 to indicate, and allow compensation for, any losses occurring in the optical sensor. This is important in that the output of the sensor is a simple power measurement relied upon as being proportional to the refractive index of the fluid, so that any losses will reduce the detected power and give an erroneous indication of index. In particular, compensation can be made for absorption and scattering losses in the fluid, which can vary with fluid type, wavelength, temperature, etc.

When designing a sensor according to the present invention, one should preferable consider a number of factors. These include operating wavelength, the refractive index and dimensions of the various waveguiding layers, and the wavelength filtering responses of the gratings. The sensitivity of the sensor to refractive index difference of the fluid depends on how much the effective modal index is affected by the index of the fluid, which in turn depends on the amount by which the optical mode of the propagating light extends out of the waveguide layers of the sensing grating and into the fluid. Thus, control of the proximity of the fluid to the waveguide mode alters the sensitivity, and also the loss of the optical mode due to absorption in the fluid. The penetration of light into an area of lower index depends on the index difference (between the waveguide and the liquid), and the wavelength of the light. In general, longer wavelengths will penetrate further into the fluid, and hence can give higher sensitivity. However, longer wavelengths may also lead to higher loss in some cases. For example, light with a wavelength of 1.3 µm may be preferable to 1.5 µm for use with water-based fluid samples due to the considerably lower absorption at the shorter wavelength.

The design should also take into account the index or range of indices of the fluid or fluids that the sensor is intended to measure. Typically, a waveguide can be expected to have a higher index than a fluid so that the optical mode will be confined to the core and there will be little penetration into the fluid. As the refractive index of the fluid approaches that of the core the penetration depth of the mode will increase, and so will the sensitivity of the sensor to the index of the fluid. For high sensitivity, it may even be appropriate to make the sensing grating waveguide of a material with an index lower than that of the fluid. This will lead to a lossy mode but will be very sensitive to the index of the fluid.

In a further embodiment, a graded index waveguide can be used for the sensing grating. The sample window comprises a region in which the waveguide containing the sensing grating is modified to bring the fluid sample into closer proximity with the evanescent field of light propagating in the waveguide, by removing part or all of the cladding of the waveguide and possibly part of the waveguide core as well (this is discussed further below). The window section of the waveguide thus has a different modal index from the adjacent parts of the waveguide, particularly if the cladding is removed completely to expose the core. The change in modal index is abrupt, which results in strong Fabry-Perot type fringes in the grating response. This affects the overlap of the response with that of the analysing grating, and hence perturbs the output of the sensor. This can be addressed by varying the refractive index of the waveguide of the sensing grating along its length, to give a graded or tapered refractive index structure. This is modifies the modal index and if suitably positioned with respect to the window, can compensate for the abrupt change in modal index caused by the window, either completely or by making the change more gradual so that the fringes are less significant. For example, the taper can extend over a distance of hundreds of micrometres to a few millimetres as required, depending on the size of the window, the depth of the removed cladding and the refractive index values of the cladding and core.

For planar gratings, optimisation of the waveguiding structure to allow single mode operation of the grating is beneficial. In general, single moded waveguides (possibly allowing for two orthogonal polarisations) will give more clearly defined reflection peaks or transmission dips in the wavelength responses of a grating. Hence, it is preferable for the waveguiding structure of the sensor to support single mode operation, particularly where the waveguide enters the sample window of the sensing grating. The fluid sample in the window may have a considerably lower refractive index than the cladding material that has been removed to form the window, which can allow the waveguide to become multimoded in the window region.

Figure 11:
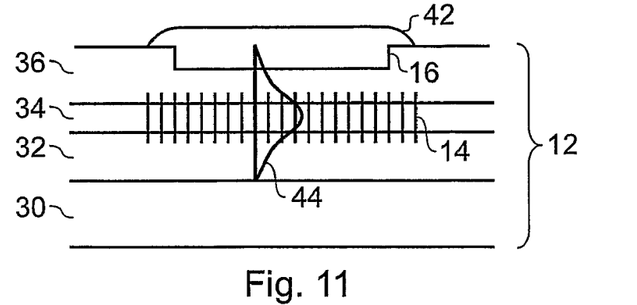
FIG. 11 shows a cross-sectional schematic representation of an optical sensor according to a further embodiment with a first configuration of a sample window.

Any waveguide configuration that offers single mode operation may be used. One design regime for addressing this issue is illustrated in FIG. 11. This shows a schematic representation of a sensor in cross-section through the length of the sensing grating. The sensor is formed from a substrate 12 comprising a base layer 30 supporting a lower cladding layer 32 underneath a core layer 34 underneath an upper cladding layer 36. The sensing grating 14 is defined in the core layer 34. The sample window 16 is located over the grating 14, and is formed by partial removal of the upper cladding layer overlying the grating 14 so that the cladding layer is thinner in this region than adjacent portions of the cladding layer. A sample of fluid 42 has been applied to the sample window 16. The portion of cladding in the sample window has been left relatively thick, however, so that the fluid is kept relatively remote from the core. This means that only a small portion of the evanescent field 44 of the propagating light penetrates into the fluid 42, so that the fluid has little impact on the modal profile and single mode operation is maintained.

Figure 12:
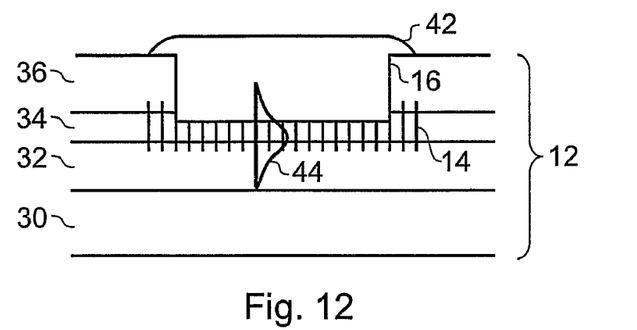
FIG. 12 shows a cross-sectional schematic representation of an optical sensor according to a further embodiment with a second configuration of a sample window.

An alternative design regime is shown in FIG. 12. Again, this shows a schematic representation of a sensor in cross-section through the length of the sensing grating, the sensor being formed on a substrate 12 having the same structure as shown in FIG. 11. In this case, however, the sample window 16 is formed by total removal of the upper cladding layer 36 in the window region and also partial removal of the core 34, so that the core 34 has a reduced thickness in the window region compared to adjacent parts of the core. This change in core thickness maintains single mode operation, and provides a more sensitive device than that of FIG. 11. However, higher losses from absorption and scattering are likely owing to the larger proportion of the evanescent field 44 that extends into the fluid 42.

Figure 13:
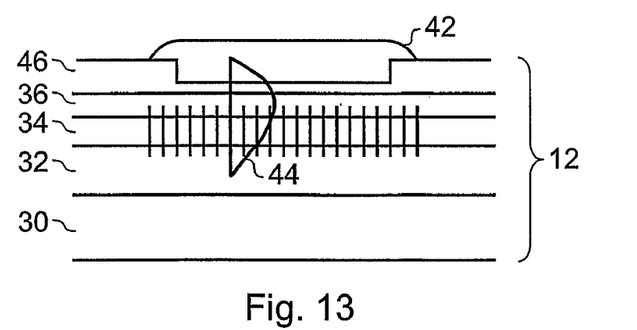
FIG. 13 shows a cross-sectional schematic representation of an optical sensor according to a further embodiment employing a layered waveguide structure.

The amount of penetration of the optical field into the fluid can also be modified by the use of one or more additional layers in the waveguide structure to tailor the modal properties of the waveguide of the sensing grating. For example, a high-index layer added to the cladding can be used to pull the optical field closer to the liquid to enhance sensitivity. Indium tin oxide is a suitable material for this [8], but other high index materials are not excluded. FIG. 13 shows a schematic representation of an example sensor designed in this way, again depicted as a cross-section through the length of the sensing grating. The sensor is fabricated on a substrate having a layered structure as previously described with reference to FIG. 11, with a sample window 16 formed by partial removal of the upper cladding layer 36 but further including an additional upper cladding layer 46 that distorts the evanescent field 44 towards the fluid 42.

Sensors according to the present invention as described above may be used to measure the bulk refractive index of fluid samples, either as a parameter of direct interest or as an indicator of a further characteristic, such as concentration. However, in other embodiments, a surface treatment may be used to allow specificity to a particular molecule of a biological agent. To achieve this, a surface coating of a chemically selective material is applied to the sample window. The chemically selective material is such that it contains receptors that bind to a specific molecular species that may be present in a fluid sample. The binding process causes a specific change in the effective modal index that can be measured as described above. Thus, a sample containing the molecular species will give a particular output from the sensor, whereas a sample lacking the molecular species will not bind to the chemically selective material and hence not modify the index in the required manner, thus giving a different output. This technique can be used for chemical and biochemical sample testing and detecting. For example, the receptors may be molecules that bind ligands present in the sample, or the receptors may be antibodies that bind antigens in the sample, or vice versa [9].

In a further embodiment, a metallic film can be applied to the sample window as a surface layer or coating. This gives a sensor that operates as a surface plasmon sensor, in which the metallic layer supports a surface plasmon that is modified by the presence of a fluid in the sample window. This modification produces a corresponding change in the effective modal index, which can be measured as described above owing to the resulting change in the Bragg wavelength of the sensing grating. Any metal that supports surface plasmons can be used, such as gold, silver, aluminium and platinum. Gold is particularly suitable for testing biological fluid samples since it is biologically compatible. Also, gold is expected to increase the sensitivity of the sensor.

Figure 14:
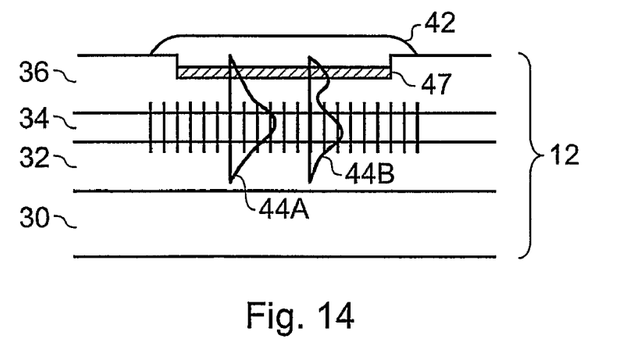
FIG. 14 shows a cross-sectional schematic representation of an optical sensor according to a further embodiment with a third configuration of a sample window.

FIG. 14 shows a schematic representation of an example sensor having a structure for chemically selective sensing or surface plasmon sensing, again depicted as a cross-section through the length of the sensing grating. The sensor is fabricated on a substrate having a layered structure as previously described with reference to FIG. 11. In this case, however, a surface coating or layer 47 is applied over the sample window, so that a fluid sample 42 sits on top of the coating. The coating 47 is a chemically selective material capable of binding with molecules in the fluid sample 42 in the case of a chemically selective sensor, or a metallic film in the case of a surface plasmon sensor. In the former case, the evanescent wave 44A is substantially undistorted compared to there being no coating. In the latter case the wave 44B has subsidiary peak in the metallic film owing to the surface plasmon; this increases the sensitivity owing to a greater proportion of the optical field being in close proximity to the fluid.

In some embodiments the sensor may further include fluid control elements or structures connected to the sample window and operable to deliver the fluid sample to the sample window and/or remove a sample from the sample window. This can allow automated or semi-automated testing of a plurality of samples, or allow measurements to be made on a continuous flow of fluid. The rate of flow can be controlled, and metered. Precise control over the volume of fluid in each sample can also be achieved, to improve accuracy of the index measurements. Any suitable structures can be used to achieve the fluid control, but micro-electro-mechanical systems (MEMS) are considered to be particularly advantageous [10]. MEMS allows the integration of small high quality mechanical structures, actuators and other devices on common silicon substrates. Silica is particularly suitable for fabrication of the sensor components (as discussed further below) so that the fluid control elements may be readily integrated with the optical sensor on a single substrate, giving a compact device. Further, silica is robust and biologically compatible, and can resist strong solvents and acids so is suitable for repeated chemical cleaning for sensor reuse.

Also, sensors according to the present invention are not limited to a single sensing grating-analyser grating pair. Two or more pairs of gratings can be included in a single sensor, to allow multiple simultaneous testing and/or to provide sensing gratings and windows of different types in a single sensor, to expand the functionality of the sensor. A multiple grating sensor can conveniently be implemented by providing all the gratings on a single substrate, but this is not essential.

There are many possible configurations for a multiple grating sensor. Any or all of the above embodiments can be integrated in a single sensor. For example, each sensing grating and sample window can be identical, to allow simultaneous testing of a plurality of samples for the same or similar parameter. A range of different sensing gratings and/or sample windows can be provided, for example gratings with different Bragg wavelengths, or configurations with different sensitivities, or windows with different chemically selective coatings (for testing a single biological sample for different compounds, for example) or windows with different surface plasmon metallic films, or any combination of these. A range of different grating wavelengths might include gratings at 1100 nm, 1200 nm, 1300 nm, 1400 nm, 1500 nm and 1600 nm, for example. This allows information to be collected as to how index varies with wavelength (dispersion $dn/d\lambda$). Also, information can be gained by analysing the changes to the grating responses from molecules in the samples. For example, the addition of water to another liquid may cause greater changes at 1400 nm and 1500 nm from the OH bonds than at 1100 nm and 1200 nm. Similarly, the presence of C—H bonds and C=C double bonds could be detected at different wavelengths to yield information about multiphase and multi-component liquids.

Provision of a heating element to change the temperature of the gratings in conjunction with gratings of different wavelengths allows the $dn/dT$ measurements described earlier to be extended into the wavelength regime so that measurements of $d(dn/dT)/d\lambda$ and $d(dn/d\lambda)/dT$ can be made.

The sensitivity can be varied from grating to grating by varying the thickness of the cladding layer in the sample windows to give different penetration depths of the optical field into the fluid sample. As well as giving different sensitivities, the different penetration depths allow different depths in a fluid sample to be interrogated to investigate layers within a sample. For example, it may be that the fluid adheres to the surface of the window (perhaps if a chemically selective coating is included) and gives a different index to the bulk of the fluid sample. A range of cladding thicknesses can be combined with gratings with different Bragg wavelengths. The gratings could have widely spaced wavelengths, as in the preceding paragraph, or alternatively, a selection of different gratings of very closely spaced wavelength (2 nm separation, for example), each with a different cladding thickness, could be used to obtain information about the build-up of molecular species. The closely spaced wavelengths have substantially the same modal confinement and hence field penetration depth and can "see" the same molecular species, but can be distinguished in detection to allow each grating to be analysed separately. Further groups of gratings with wavelengths closely spaced around a wavelength more widely spaced from the first group can be provided to give a spectral dimension to the measurements.

Figure 15:
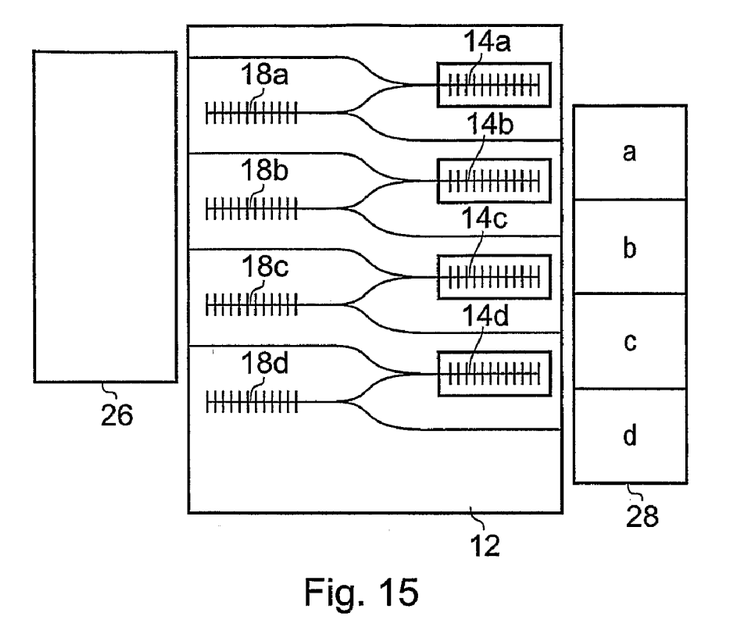
FIG. 15 shows a schematic representation of an optical sensor according to a further embodiment of the present invention that incorporates multiple gratings.

FIG. 15 shows a schematic plan view representation of a multiple grating sensor. Four grating pairs a, b, c and d are included, each configured with both the sensing grating 14 and the analysing grating 18 used in reflection (other combinations of reflection and/or transmission can be used). All gratings and their associated waveguides are arranged on a single substrate 12. In this example, the light source 26 comprises a single LED (which may be a superluminescent LED, for example) arranged to couple light into all of the input waveguides. The light source should generate light covering the total combined bandwidth of all the gratings in the sensor. In the case of gratings with different Bragg wavelengths, a single broadband source is convenient, although different sources can be used for different gratings if desired or necessary. The filtering nature of the gratings makes them self-selective with respect to wavelength, so each can receive light with the same spectrum so long as that spectrum covers all the grating responses. Also in this example, the optical power detector 28 comprises an array of photodiodes a, b, c and d, one for each grating pair. This allows each grating pair to be used simultaneously. If non-simultaneous operation is preferred, a single re-positionable photodetector might be deemed adequate.

A sensor with multiple gratings may further include reference windows provided for some or all of the analyser gratings, as discussed above with regard to the embodiments having a single grating pair only. Further with regard to the fluid receiving windows, multiple grating sensors which are intended for measurement of the same fluid at different wavelengths may be implemented with a single common sample window that extends over all of the sensing gratings. This allows a single fluid sample to be applied to all the sensing gratings at one time, making measurements simpler and more convenient to make, and also simplifying fabrication of the sensor. Multiple grating sensors having sensing gratings with different cladding thicknesses can also employ a single sample window, for example by stepping the cladding layer from grating to grating over the extent of the window, or having individual regions of different cladding thickness connected by fluid channels to form a single fluid-receiving region. Similarly, if the analyser gratings are provided with reference windows, a single window covering all the analyser gratings can be provided to allow the same reference fluid to be conveniently applied to all the analyser gratings.

Figure 16:
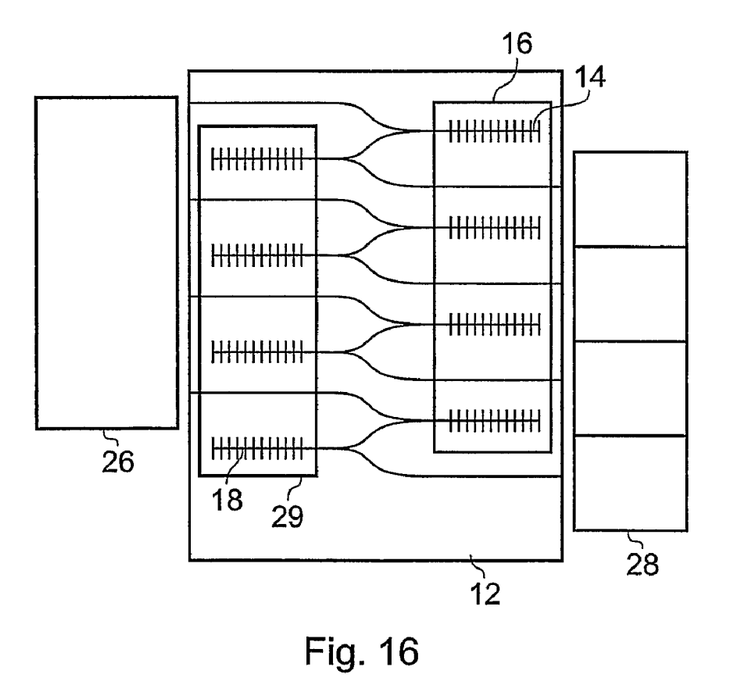
FIG. 16 shows a schematic representation of an optical sensor according to a further embodiment of the present invention that incorporates multiple gratings with shared windows.

FIG. 16 shows a schematic plan view of a multiple grating sensor in which the gratings are arranged for use in reflection as in FIG. 16, but in which a single sample window 16 is provided for all the sensing gratings 14, and a single reference window 29 is provided for all the analysing gratings 18.

Any fabrication techniques suitable for making gratings and waveguides and connecting them in the required manner can be employed to fabricate optical sensors according to the invention described thus far. For example, lithography and etching may be used. A particularly suitable technique is that of direct ultraviolet (UV) writing, using UV laser radiation to increase the refractive index of silica to write both channel waveguides and gratings into a single substrate [11].

The direct UV writing fabrication technique is particularly advantageous because it allows long high quality planar gratings to be written. This gives gratings with a very narrow linewidth, leading to sensors with high sensitivity. The bandwidth $\Delta\lambda$ of a Bragg grating of Bragg wavelength $\lambda_{Bragg}$ is given by [12]:

$$\Delta\lambda = \lambda^2_{Bragg}/2n_{eff}L(\pi^2+(\kappa L)^2)^{1/2}$$

where $\kappa$ is the coupling coefficient defined by $$\kappa = \pi n \delta n \eta / \lambda_{Bragg} n_{eff}$$

and n is the refractive index of the waveguide cladding, $n_{eff}$ is the effective modal index, $\delta n$ is the magnitude of the index modulation in the grating, $\eta$ is the overlap integral between forward and backward propagating modes, and L is the length of the grating. Thus, the bandwidth depends on the length of the grating for weak gratings and on the index modulation for stronger gratings. The resolution of the optical sensor to fluid refractive index change is related to the minimum resolvable wavelength shift, and thus it is desirable to use long gratings with narrow spectral bandwidths (wavelength filtering response).

Some example sensors have been fabricated using the direct UV writing technique to write channel waveguides and gratings into a silica on silicon three layer wafer. This has an underlying silicon wafer base that provides a robust carrier for subsequent deposition of doped silicon oxide (doped silica) to form the various waveguiding layers. Silicon is compatible with processing for the growth and annealing of oxide layers. In addition it is possible to incorporate other elements into the silicon wafer, such as MEMS structures for flow control, metering and heating of fluid samples, and for additional integrated measurements such as in-situ thermal measurements. Also, a silicon wafer has a lower thermal expansion coefficient than silica, so that after annealing the silica layers are under compressive stress at room temperature, which helps to make the layers robust. It is, however, possible to grow the silica layers on materials other than silicon, including but not limited to silica.

The layers can be grown by a number of techniques. The starting point is the silicon base which is conventionally thermally oxidised in a steam environment to grow a thin oxide layer on its surface. This first layer helps the growth and consolidation of the later, thicker oxide layers. These layers may be deposited using techniques such as flame hydrolysis deposition (FHD), low pressure chemical vapour deposition (LPCVD), plasma enhanced chemical vapour deposition (PECVD), direct bonding or ion exchange. For direct UV writing, a photosensitive layer is required. This may be achieved with a three-layer structure in which the upper and lower layers are cladding layers and the central layer is a core layer that is doped with a material to promote sensitivity such as germanium oxide. Any of the layers may also include additional dopants to control refractive index, fabrication temperature, etc. Commonly, phosphorus, boron, tin and titanium are doped into silica. Also, doping the layers with deuterium at high pressure for several days can be used to increase the photosensitive response. Hydrogen is an alternative photosensitiser. Alternatively, rapid thermal processing can be employed to increase photosensitivity.

Next, channel waveguides are written into the layered substrate. For direct UV writing, a substrate is translated under a focussed. spot of UV laser radiation, the spot having dimensions approximately related to the desired channel dimensions. Preferably, the channels are designed to be single mode to give a strong Bragg grating response. The gratings are defined using a spot with an intrinsic interference pattern. The laser intensity is modulated at precisely controlled positions, allowing a grating to be written simultaneously with the waveguide containing it. Computer control of the writing apparatus allows precise control of the grating period and length (and hence Bragg wavelength and bandwidth) and optical waveguide shape. Thus, single-substrate optical sensors comprising one or more pairs of gratings connected by channel waveguides such as those described above can be written with a single fabrication process.

After waveguide and grating formation, the substrate is processed to form the sample window or windows. Etching with hydrofluoric acid can be used to remove the cladding material. The window region is defined by masking the non-window parts of the substrate with photoresist, before etching. The photoresist may be defined using lithographic processes that are related to the positioning of the waveguides to place the windows in correct registration with the grating positions. If several windows with different cladding depths are required, the window regions can be etched to different depths using techniques such as depositing differently etch-resistant layers before etching, suspending etching at appropriate times and covering sufficiently etched windows with etch-resistant material, lowering the substrate into an etching liquid in steps, or pulling a masking plate across the substrate in steps in the case of gas phase etching.

The example sensors were fabricated as described above. For operation, the sensors were connected to an amplified spontaneous emission (ASE) source producing broadband light centred around 1550 nm. The light was polarised so that birefringence in the waveguides did not cause a splitting of the grating responses; this may or may not be found necessary for a given sensor. Further, the polarisation was in the TE orientation to reduce optical loss. The sensor output was recorded using an optical spectrum analyser, but the spectral resolution provided thereby is not required; a simple detector capable of detecting power only is suitable.

The present invention is not limited to optical sensors comprising planar Bragg gratings coupled by channel waveguides all on a single substrate, however. Optical fibres or free-space optical transmission may be used to carry light between optical sources, gratings and detectors, and/or the gratings may be on separate substrates. Further, the gratings need not be planar gratings. Fibre Bragg gratings could be used instead, possible using fibres and fibres couplers to connect the gratings to give an all-fibre optical sensor. Furthermore, there is no requirement for gratings of any kind. Either or both of the sensing grating and the analyser grating may be replaced by other wavelength selective filtering elements having wavelength filtering responses, so long as there is a way in which a fluid sample can be applied to one of the elements (the sensing element) in a way that causes the refractive index of the fluid to alter the wavelength filtering response of that element. There is no need for the filtering element adding as the analysing element to have a wavelength filtering response that is variable in the way that a Bragg grating response is variable, although if fixed, there will be no inherent compensation against external variables such as temperature that may alter the response of the sensing element.

REFERENCES

[1] J Bowen, L J Noe, B P Sullivan, K Morris, V Martin and G Donnelly, "Gas phase detection of trinitrotoluene utilizing a solid-phase antibody immobilized on a gold film by means of surface plasmon resonance spectroscopy", Appl. Spectrosc., 57(8), 906-914, 2003.

[2] R G Heideman, R P H Kooyman and J Greve, "Performance of a highly sensitive optical wave-guide Mach-Zehnder interferometer immunosensor", Sensors and Actuators B-Chemical, 10(3), 209-217, 1993.

[3] K Tiefenthaler and W Kukosz, "Integrated optical switches and gas sensors", Optics Letters, 10(4), 137-139, 1984.

[4] W Lukosz, D Clerc and PhM Nellen, "Input and output grating couplers as integrated optical chemo- and biosensors", Sensors and Acuators A, 25-27, 181-184, 1991.

[5] A Asseh, S Sandgren, H Ahlfeldt, B Sahlgren, R Stubbe and G Edwall, "Fiber optical Bragg grating refractometer", Fiber and Integrated Optics, 17(1), 51-62, 1998.

[6] A Iadicicco, A Cusano, A Cutolo, R Bemini and M Giordano, "Thinned fiber Bragg gratings as high sensitivity refractive index sensor", IEEE Photonics Technology Letters, 16(4), 1149-1151, 2004.

[7] X Chen, K Zhou, L Zhang and I Bennion, "Optical chemsensors utilizing long-period fiber gratings UV-inscribed in D-fiber with enhanced sensitivity through cladding etching", IEEE Photonics Technology Letters, 16(5), 1352-1354, 2004.

[8] B J Luff, J S Wilkinson, G Perrone, "Indium tin oxide overlayered waveguides for sensor applications", Applied Optics, 36(27), 7066-7072, 1997.

[9] W Lukosz, "Integrated optical chemical and biochemical sensors", Sensors and Actuators B, 29, 37-50, 1995.

[10] M Q Bu, M Tracy, G Ensell, J S Wilkinson, A G R Evans, "Design and theoretical evaluation of a novel microfluidic device to be used for PCR", Journal of Micromechanics and Microengineering, 13(4), S125-S130, 2003.

[11] GB 2 395 797

[12] R Kashyap, "Photosensitive optical fibers: Devices and applications", Optical Fiber Technology, 1, 17-34, 1994.

The invention claimed is:

1. An optical sensor comprising:
a sensing element comprising:
a first wavelength selective filter having a first wavelength filtering response that varies with an effective modal index experienced by light propagating in the filter; and
a sample window arranged to receive a sample of fluid such that the presence of a sample of fluid affects the effective modal index experienced by light propagating in the filter and hence modifies the first wavelength filtering response;
the sensing element arranged to receive light from a light source and to output the light after filtering; and
an analysing element comprising a second wavelength selective filter having a second wavelength filtering response, wherein the second wavelength filtering response overlaps with the first wavelength filtering response, and wherein the analysing element is arranged to receive light output by the sensing element and to output the light after filtering in dependence on the extent of the overlap of the first and second wavelength filtering responses for detection by an optical power detector.

2. An optical sensor according to claim 1, in which the sensing element is arranged such that it outputs light that has been filtered by reflection from the first wavelength selective filter.

3. An optical sensor according to claim 1, in which the sensing element is arranged such that it outputs light that has been filtered by transmission through the first wavelength selective filter.

4. An optical sensor according to claim 1, in which the analysing element is arranged such that it outputs light that has been filtered by reflection from the second wavelength selective filter.

5. An optical sensor according to claim 1, in which the analysing element is arranged such that it outputs light that has been filtered by transmission through the second wavelength selective filter.

6. An optical sensor according to claim 1, in which the sensing element and the analysing element comprise planar waveguides containing gratings of periodic refractive index change that define the wavelength selective filters.

7. An optical sensor according to claim 6, in which the waveguides are configured for single mode propagation of light.

8. An optical sensor according to claim 6, in which the sample window overlies the grating of the sensing element and comprises a portion of a cladding layer overlying a core of the waveguide of the sensing element, such that a sample of fluid received by the sample window is in contact with the cladding layer.

9. An optical sensor according to claim 6, in which the sample window overlies the grating of the sensing element and comprises an exposed portion of a core of the waveguide of the sensing element, such that a sample of fluid received by the sample window is in contact with the core.

10. An optical sensor according to claim 9, in which the exposed portion of the core has a thickness less than a thickness of the core in adjacent portions of the waveguide of the sensing element.

11. An optical sensor according to claim 6, in which a core of the waveguide of the sensing element has a tapering variation in refractive index along its length, to reduce abrupt changes in the effective model index between the exposed portion of the core and adjacent portions of the core.

12. An optical sensor according to claim 6, in which the waveguide of the sensing element comprises one or more layers that modify waveguiding properties of the waveguide.

13. An optical sensor according to claim 1, in which the sample window is provided with a surface coating of a chemically selective material operable to bind with molecules that may be present in a sample of fluid to be received by the sample window, the binding causing an alteration of the effective modal index.

14. An optical sensor according to claim 1, in which the sample window is provided with a surface layer of a metal having a surface plasmon that may be altered by a sample of fluid to be received by the sample window, the alteration in the surface plasmon causing an alteration of the effective modal index.

15. An optical sensor according to claim 1, and further comprising:

a substrate on which the sensing element and the analysing element are positioned;
an input waveguide defined on the substrate and arranged to deliver light from a light source to the sensing element;
a connecting waveguide defined on the substrate and arranged to deliver light output by the sensing element to the analysing element; and
an output waveguide defined on the substrate and arranged to deliver light output by the analysing element for detection by an optical power detector.

16. An optical sensor according to claim 15, in which the connecting waveguide is arranged to deliver a portion of light output by the sensing element to the analysing element and further arranged to deliver a portion of light output by the sensing element for detection by an optical power detector.

17. An optical sensor according to claim 15, and further comprising one or more fluid flow control elements positioned on the substrate and operable to supply fluid to and/or remove fluid from the sample window.

18. An optical sensor according to claim 17, in which the fluid flow control elements are micro-electro-mechanical systems (MEMS) devices.

19. An optical sensor according to claim 15, and further comprising one or more additional sensing elements positioned on the substrate, each additional sensing element having an associated analysing element positioned on the substrate and associated input, connecting and output waveguides defined on the substrate.

20. An optical sensor according to claim 19, in which each sensing element has a substantially identical first wavelength filtering response.

21. An optical sensor according to claim 19, in which each sensing element or group of sensing element has a different first wavelength filtering response.

22. An optical sensor according to claim 21, in which the different first wavelength filtering responses have different centre wavelengths.

23. An optical sensor according to claim 19, in which each sensing element comprises a planar waveguide containing a grating of periodic refractive index change that defines the first wavelength selective filter of that sensing element, and the sample window of each sensing element overlies the grating of that sensing element and comprises a portion of a cladding layer overlying a core of the waveguide of that sensing element, such that a sample of fluid received by the sample window is in contact with the cladding layer,
in which the portion of the cladding layer of each sensing element or group of sensing elements has a different thickness.

24. An optical sensor according to claim 19, in which the sensing elements comprise a single sample window shared by the sensing elements such that a sample of fluid received by the single sample window modifies the wavelength filtering response of each sensing element.

25. An optical sensor according to claim 1 and further comprising one or more light sources operable to deliver light to the or each sensing element such that the or each sensing element receives light having a spectral bandwidth covering at least part of its first wavelength filtering response.

26. An optical sensor according to claim 25, in which the one or more light sources comprise a single light source.

27. An optical sensor according to claim 1, and further comprising an optical power detector operable to detect the optical power of light output by the or each analysing element.

28. A method of measuring refractive index comprising:
placing a sample of fluid having a refractive index in proximity to a first wavelength selective filter having a first wavelength filtering response that varies with an effective modal index experienced by light propagating in the filter and is modified by the presence of the sample of fluid;
applying light to the first wavelength selective filter to obtain an output of light filtered by the first wavelength selective filter;
applying the light output by the first wavelength selective filter to a second wavelength selective filter having a second wavelength filtering response, with the second wavelength filtering response overlapping with the first wavelength filtering response, and wherein the analysing element is to obtain an output of light filtered by the second wavelength selective filter in dependence on the extent of the overlap of the first and second wavelength filtering responses;
making an optical power measurement of the light output by the second wavelength selective filter, the optical power being proportional to the refractive index of the sample of fluid; and
deducing the refractive index of the sample of fluid from the optical power measurement.

29. A method according to claim 28, and further comprising deducing a characteristic of the sample of fluid from the deduced refractive index where that characteristic is related to refractive index.

30. An optical sensor comprising:
a sensing element comprising:
a first wavelength selective filter having a first wavelength filtering response that varies with an effective modal index experienced by light propagating in the filter; and
a sample window arranged to receive a sample of fluid such that the presence of a sample of fluid affects the effective modal index experienced by light propagating in the filter and hence modifies the first wavelength filtering response;
the sensing element arranged to receive light from a light source and to output the light filtering; and
an analysing element comprising a second wavelength selective filter having a second wavelength filtering response, and arranged to receive light output by the sensing element and to output the light after filtering for detection by an optical power detector; and wherein the analysing element further comprises a reference window arranged to receive fluid such that the presence of fluid affects an effective modal index of light propagating in the second wavelength selective filter and modifies the second wavelength filtering response.

31. An optical sensor comprising:
a sensing element comprising:
a first wavelength selective filter having a first wavelength filtering response that varies with an effective modal index experienced by light propagating in the filter; and
a sample window arranged to receive a sample of fluid such that the presence of a sample of fluid affects the effective modal index experienced by light propagating in the filter and hence modifies the first wavelength filtering response;
the sensing element arranged to receive light from a light source and to output the light after filtering;
an analysing element comprising a second wavelength selective filter having a second wavelength filtering response, and arranged to receive light output by the sensing element and to output the light after filtering for detection by an optical power detector;

a substrate on which the sensing element and the analysing element are positioned;

an input waveguide defined on the substrate and arranged to deliver light from a sight source to the sensing element;

a connecting waveguide defined on the substrate and arranged to deliver light output by the sensing element to the analysing element;

an output waveguide defined on the substrate and arranged to deliver light output by the analysing element for detection by an optical power detector; and a heater operable to modify the temperature of the sensing element and the analysing element such that the sensing element and the analysing element have substantially the same temperature.

* * * * *